(12) United States Patent
Reubinoff et al.

(10) Patent No.: US 6,875,607 B1
(45) Date of Patent: Apr. 5, 2005

(54) EMBRYONIC STEM CELLS

(75) Inventors: Benjamin Eithan Reubinoff, Elsternwick (AU); Martin Frederick Pera, Prahran (AU); Chui-Yee Fong, Singapore (SG); Alan Osborne Trounson, Asburton (AU); Ariffeen Bongso, Singapore (SG)

(73) Assignee: ES Cell International Pte Ltd, Singapore (SG)

( * ) Notice: Subject to any disclaimer, the term of this patent is extended or adjusted under 35 U.S.C. 154(b) by 0 days.

(21) Appl. No.: 09/436,164

(22) Filed: Nov. 9, 1999

(30) Foreign Application Priority Data

Nov. 9, 1998 (AU) .............................................. PP7009
Sep. 15, 1999 (AU) .............................................. PQ2852

(51) Int. Cl.$^7$ ........................... A01N 1/00; C12N 5/00; C12N 5/02
(52) U.S. Cl. ...................................... 435/325; 435/1.1
(58) Field of Search ...................... 435/325, 1.1; 800/8

(56) References Cited

U.S. PATENT DOCUMENTS

| | | | | |
|---|---|---|---|---|
| 5,843,780 A | * | 12/1998 | Thomson | 435/363 |
| 6,200,806 B1 | * | 3/2001 | Thomson | 435/366 |
| 6,280,718 B1 | * | 8/2001 | Kaufman et al. | 424/93.1 |

FOREIGN PATENT DOCUMENTS

| | | |
|---|---|---|
| WO | WO96/22362 | 7/1996 |
| WO | WO97/32033 | 9/1997 |
| WO | WO 98 0784 1 | 2/1998 |
| WO | WO98/43679 | 10/1998 |

OTHER PUBLICATIONS

JA Thomson et al., TIBTECH, "Human embryonic stem cell and embryonic germ cell lines," Feb. 2000, vol. 18, pp. 53–57.*

J Nichols et al., Development, "Establishment of germ-line-competent embryonic stem (ES) cells using differentiation inhibiting activity," 1990,110, pp. 1341–1348.*

AJ Clark et al., Transgenic Animals, "Germ line manipulation: applications in agriculture and biotechnology," pp. 249–250.*

JA Piedrahita et al., Theriogenology, "On the Isolation of Embryonic Stem Cells: Comparative Behavior of Murine, Porcine and Ovine Embryos," Nov. 1990, vol. 34, No. 5, pp. 879–901.*

JS Odorico et al., Stem Cells, "Multilineage Differentiation from Human Embryonic Stem Cell Lines," 2001; 19:193–204.*

YP Cruz et al., Animal Applications of Research in Mammalian Development, "Origin of Embryonic and Extraembryonic Cell Lineages in Mammalian Embryos," pp. 147–204.*

Bongso, A., et al. (1994) "The Growth of Inner Cell Mass Cells From Human Blastocysts", Theriogenology, Los Altos, CA, US, vol. 41, pp. 167.

Pera, M.F., et al. (1999) "Human Embryonic Stem Cells", Journal of Cell Science, Essex, GB, vol. 113, pp. 5–10.

Reubinoff, B.E., et al. (2000) "Embryonic Stem Cell Lines from Human Blastocysts: Somatic Differentiation in Vitro", Nature Biotechnology, vol. 18, No. 4, pp. 399–404.

Thomas, J.A., et al., "Neural Differentation of Rhesus Embryonic Stem Cells", Apmis, Copenhagen, DK, vol. 106, 1998, pp. 149–156.

Li F., et al., "Hematopietic Differentiation In Vitro of Rhesus Monkey Embryonic Stem Cells", Blood, W.B. Saunders, Philadelphia, VA, US, vol. 92, No. 10 Suppl. 1, par. 15, Nov. 1998, p. 368A.

Rathjen, P.D., et al., "Properties and Uses of Embryonic Stem Cells: Prospects for Application to Human Biology and Gene Therapy", Reproduction and Fertility and Development, CSIRO, East Melbourne, AU, vol. 19, No. 1, pp. 31–47.

Pederson, R.A., "Studies of In Vitro Differentation with Embryonic Stem Cells", Reproduction, Fertility and Development, CSIRO, East Melbourne, AU, vol. 6, No. 5, 1994, pp. 543–552.

Brook, F.A., et al., "The Origin and Efficient Derivation of Embryonic Stem Cells in the Mouse", Proceedings of the National Academy of Sciences of USA, National Academy of Science, Washington, US, vol. 94, May 1997, pp. 5709–5712.

Evans, M. J., et al., (1981) "Establishment in culture of pluripotential cells from mouse embryos", Nature 292:154–156.

Martin, G. R., (1981) "Isolation of a pluripotent cell line from early mouse embryos cultured in medium conditioned by teratocarcinoma stem cells", Proc. Natl. Acad. Sci USA 78(12):7634–7638.

Andrews, P. W., et al. (1984) "Pluripotent Embryonal Carcinoma Clones Derived from the Human Teratocarcinoma Cell Line Tera–2", Lab. Invest. 50(2):147–162.

(Continued)

Primary Examiner—Joseph Woitach
(74) Attorney, Agent, or Firm—Scully, Scott, Murphy & Presser

(57) ABSTRACT

The present invention relates to undifferentiated human embryonic stem cells, methods of cultivation and propagation, production of differentiated cells and in particular the production of human embryonic stem cells capable of yielding somatic differentiated cells in vitro, as well as committed progenitor cells capable of giving rise to mature somatic cells and uses thereof. The present invention also provides a purified preparation of undifferentiated human embryonic stem cells capable of proliferation in vitro. Furthermore, the present invention provides a somatic cell differentiated in vitro from an undifferentiated embryonic stem cell. There is also provided a committed progenitor cell capable of giving rise to mature somatic cells.

8 Claims, 7 Drawing Sheets

OTHER PUBLICATIONS

Pera, M. F., et al. (1989) "Isolation and characterization of a multipotent clone of human embryonal carcinoma–cells", *Differentiation 42:*10–23.

Thomson, J. A., et al. (1995) "Isolation of a primate embryonic stem cell line", *Proc. Natl. Acad. Sci USA 92:*7844–7848.

Thomson, J. A., et al. (1996) "Pluripotent Cell Lines Derived from Common Marmoset (*Callithrix jacchus*) Blastocysts", *Bio Reprod. 55:*254–259.

Bongso, A., et al. (1994) "Isolation and culture of inner cell mass cells from human blastocysts", *Hum. Reprod. 9(11):*2110–2117.

Andrews, P. W., et al. (1996) "Comparative analysis of cell surface antigens expressed by cell–lines derived from human germ cell tumours", *Int. J. Cancer 66:*806–816.

Cooper, S., et al. (1992) "A novel keratan sulfate proteoglycan from a human embryonal carcinoma cell line", *Biochem.J. 286:*959–966.

Pera, M. F., et al. (1988) "Analysis of cell–differentiation lineage in human teratomas using new monoclonal antibodies to cytostructural antigens of embryonal carcinoma cells", *Differentiation 39:*139–149.

Fong, C. Y., et al. (1998) "Comparison of human blastulation rates and total cell number in sequential culture media with and without co–culture", *Hum. Reprod. 14(3):*774–781.

Fong, C. Y., et al. (1997) "Ongoing normal pregnancy after transfer of zona–free blastocyts: implications for embryo transfer in the human", *Hum. Reprod. 12(3):*557–560.

Solter, D., et al. (1975) "Immunosurgery of mouse blastocyst", *Proc. Natl Acad Sci USA 72(12):*5099–5102.

Vajta, G., et al. (1998) "Open Pulled Straw (OPS) Vitrification: A New Way to Reduce Cryoinjuries of Bovine Ova and Embryos", *Molecular Reproduction and Development 51:*53–58.

Vajta, G., et al. (1998) "Sterile application of the opened pulled straw (OPS) vitrification method", *Cryo–letters 19:*389–392.

Kleinsmith, L. J., et al. (1964) "Multipotentiality of Single Embryonal Carcinoma Cells", *The University of Michigan 24:*1544–1551.

Stevens, L. C. (1983) "Testicular, ovarian, and embryo-derived teratomas", *Cancer Surveys 2(1):*75–91.

Martin, G. R. (1980) "Teratocarcinomas and Mammalian Embryogenesis", *Science 209:*768–776.

Matsui, Y., et al. (1992) "Derivation of Pluripotential Embryonic Stem Cells from Murine Primordial Germ Cells in Culture", *Cell 70:*841–847.

Thompson, S., et al. (1984) "Cloned human teratoma cells differentiate into neuron–like cells and other cell types in retinoic acid", *F. Cell Sci. 72:*37–64.

Pirty, M., et al., "Embryonic Stem Cells, Creating Transgenic Animals", *Methods in Cell Biology,* Academic Press, pp. 279–293.

Shamblott, M. J., et al., (1998) "Derivation of pluripotent stem cells from cultured human primordial germ cells", *Proc. Natl. Acad. Sci., 95:*13726–13731.

Svendsen, C. N., et al., (1999) "New prospects for human stem–cell therapy in the nervous system", *Trends in Neurosciences, 22(8):*357–364.

Thomson, J. A., et al., (1998) "Embryonic Stem Cell Lines Derived From Human Blastocysts", *Science, 282:*1145–1147.

* cited by examiner

EMBRYONIC STEM CELLS

The present invention relates to undifferentiated human embryonic stem cells, methods of cultivation and propagation, production of differentiated cells and in particular the production of human ES capable of yielding somatic differentiated cells in vitro, as well as committed progenitor cells capable of giving rise to mature somatic cells and uses thereof.

The production of human embryonic stem cells which can be either maintained in an undifferentiated state or directed to undergo differentiation into extraembryonic or somatic lineages in vitro allows for the study of the cellular and molecular biology of early human development, functional genomics, generation of differentiated cells from the stem cells for use in transplantation or drug screening and drug discovery in vitro.

In general, stem cells are undifferentiated cells which can give rise to a succession of mature functional cells. For example, a haematopoietic stem cell may give rise to any of the different types of terminally differentiated blood cells. Embryonic stem (ES) cells are derived from the embryo and are pluripotent, thus possessing the capability of developing into any organ, cell type or tissue type or, at least potentially, into a complete embryo.

The development of mouse ES cells in 1981 (Evans and Kaufman, 1981; Martin, 1981) provided the paradigm, and, much of the technology, for the development of human ES cells. Development of ES cells evolved out of work on mouse teratocarcinomas, (tumours arising in the gonads of a few inbred strains), which consist of a remarkable array of somatic tissues juxtaposed together in a disorganised fashion. Classical work on teratocarcinomas established their origins from germ cells in mice, and provided the concept of a stem cell (the embryonal carcinoma or EC cell) which could give rise to the multiple types of tissue found in the tumours (Kleinsmith and Pierce, 1964; review, Stevens, 1983). The field of teratocarcinoma research (review, Martin, 1980) expanded considerably in the 70's, as the remarkable developmental capacity of the EC stem call became apparent following the generation of chimaeric mice by blastocyst injection of EC cells, and investigators began to realise the potential value of cultured cell lines from the tumours as models for mammalian development. EC cells however had limitations: they often contained chromosomal abnormalities, and their ability to differentiate into multiple tissue types was often limited.

Since teratocarcinomas could also be induced by grafting blastocysts to ectopic sites, it was reasoned that it might be possible to derive pluripotential cell lines directly from blastocysts rather than from tumours, as performed in 1981 by Gail Martin and Martin Evans independently. The result was a stable diploid cell line which could generate every tissue of the adult body, including germ cells. Teratocarcinomas also develop spontaneously from primordial germ cells in some mouse strains, or following transplantation of primordial germ cells to ectopic sites, and in 1992 Brigid Hogan and her colleagues reported the direct derivation of EG cells from mouse primordial germ cells (Matsui et al., 1992). These EG cells have a developmental capacity very similar to ES cells.

Testicular teratocarcinomas occur spontaneously in humans, and pluripotential cell lines were also developed from these (review, Andrews, 1988). Two groups reported the derivation of cloned cell lines from human teratocarcinoma which could differentiate in vitro into neurons and other cell types (Andrews et al., 1984, Thompson et al., 1984). Subsequently, cell lines were developed which could differentiate into tissues representative of all three embryonic germ layers (Pera et al., 1989). As analysis of the properties of human EC cells proceeded, it became clear that they were always aneuploid, usually (though not always) quite limited in their capacity for spontaneous differentiation into somatic tissue, and different in phenotype from mouse ES or EC cells.

The properties of the pluripotent cell lines developed by Pera et al. (1989) are as follows:

Express SSEA-3, SSEA-4, TRA 1–60, GCTM-2, alkaline phosphatase, Oct-4

Grow as flat colonies with distinct cell borders

Differentiate into derivatives of all three embryonic germ layers

Feeder cell dependent; feeder cell effect on growth not reconstituted by conditioned medium from feeder cells or by feeder cell extracellular matrix Highly sensitive to dissociation to single cells, poor cloning efficiency even on a feeder cell layer Do not respond to Leukemia Inhibitory Factor These studies of human EC cells essentially defined the phenotype of primate pluripotential stem cells.

Derivation of primate ES cells from the rhesus monkey blastocyst and later from that of the marmoset (Thomson et al., 1995, 1996)has been described. These primate cell lines were diploid, but otherwise they closely resembled their nearest counterpart, the human EC cell. The implication of the monkey work and the work on human EC cells was that a pluripotent stem cell, which would be rather different in phenotype from a mouse ES cell, could likely be derived from a human blastocyst.

Bongso and coworkers (1994) reported the short term culture and maintenance of cells from human embryos fertilised in vitro. The cells isolated by Bongso and coworkers had the morphology expected of pluripotent stem cells, but these early studies did not employ feeder cell support, and it was impossible to achieve long term maintenance of the cultures.

James Thomson and coworkers (1998) derived ES cells from surplus blastocysts donated by couples undergoing treatment for infertility. The methodology used was not very different from that used 17 years earlier to derive mouse ES stem cells: the trophectoderm, thought to be inhibitory to ES cell establishment, was removed by immunosurgery, the inner cell mass was plated on to a mouse embryonic fibroblast feeder cell layer, and following a brief period of attachment and expansion, the resulting outgrowth was disaggregated and replated onto another feeder cell layer. There were no significant departures from mouse ES protocols in the media or other aspects of the culture system and a relatively high success rate was achieved. The phenotype of the cells was similar to that outlined above in the human EC studies of Pera et al.

In the studies of Thomson et al. on monkey and human ES cells, there was no evidence that the cells showed the capacity for somatic differentiation in vitro. Evidence for in vitro differentiation was limited to expression of markers characteristic of trophoblast and endoderm formation (production of human chorionic gonadotrophin and alphafoetoprotein); it is not possible to state whether the cells found producing alphafetoprotein represent extraembryonic (yolk sac) endoderm or definitive (embryonic) endoderm though the former is far more likely. Thus an essential feature for any human ES cell line to be of practical use, namely the production of differentiated somatic cells in vitro as seen in previous studies of human EC cells, was not demonstrated in the monkey or human ES cell studies.

It is an object of the invention to overcome or at least alleviate some of the problems of the prior art.

SUMMARY OF THE INVENTION

In one aspect of the present invention, there is provided a purified preparation of undifferentiated human embryonic stem cells capable of proliferation in vitro.

In another aspect, there is provided a somatic cell differentiated in vitro from an undifferentiated embryonic stem cell. There is also provided a committed progenitor cell capable of giving rise to mature somatic cells.

Preferably the undifferentiated cells have the potential to differentiate into extraembryonic and embryonic (somatic) lineages when subjected to differentiating conditions.

More preferably, the undifferentiated cells are capable of maintaining an undifferentiated state when cultured on a fibroblast feeder layer.

In another aspect of the present invention there is provided an undifferentiated human embryonic stem cell wherein the cell is immunoreactive with markers for human pluripotent stem cells including SSEA-4, GCTM-2 antigen, TRA 1–60. Preferably, the cells express the transcription factor Oct-4 as demonstrated by RT-PCR. More preferably, the cells maintain a diploid karyotype during prolonged cultivation in vitro.

In a further aspect of the present invention, there is provided a method of preparing undifferentiated human embryonic stem cells, said method including:

obtaining an in vitro fertilised human embryo and growing the embryo to a blastocyst stage of development;

removing inner cells mass (ICM) cells from the embryo;

culturing ICM cells under conditions which do not induce extraembryonic differentiation and cell death; and promote proliferation of undifferentiated cells; and recovering stem cells.

In a further preferred aspect of the present invention there is provided a method of preparing undifferentiated human embryonic stem cells, said method including:

obtaining in vitro fertilised human embryo;

removing inner cell mass (ICM) cells from the embryo;

culturing ICM cells on a fibroblast feeder layer to obtain proliferation of embryonic stern cells; and recovering stem cells from the feeder layer.

In a preferred aspect of the invention the method further includes the following steps before removal of inner cell mass cells, said steps including:

treating the embryo to dislodge the trophectoderm of the embryo or a portion thereof;

washing the embryo with an appropriate blastocysts culture medium; for example G2 or S2 (Scandinavian-2 medium) to dislodge the trophectoderm or a portion thereof; and obtaining inner cell mass cells of the embryo.

Preferably, the treatment of the embryo includes treating with an antibody or antiserum reactive with epitopes on the surface of the trophectoderm. More preferably, the treatment with antibody or antiserum is combined with treatment with complement. Most preferably, the combined antibody and complement are either anti-placental alkaline phosphatase antibody combined with Baby Rabbit complement; or anti-human serum antibody combined with Guinea Pig complement. The antibody and complement may be used together or separately to treat the embryo to dislodge the trophectoderm or a portion thereof.

In a further aspect of the invention, the method further includes:

replacing the stem cells from the fibroblast feeder layer onto another fibroblast feeder layer; and culturing the stem cells for a period sufficient to obtain proliferation of morphologically undifferentiated stem cells.

In an even further aspect of the invention the method further includes propagating the undifferentiated stem cells. The methods of propagation may initially involve removing clumps of undifferentiated stem cells from colonies of cells. This is preferably done by chemical or mechanical means. More preferably, the cells are treated chemically and washed in PBS or they are mechanically severed from the colonies or a combination of the two methods.

In another aspect of the invention there is provided a method of induction of differentiation of stem cells. This method involves cultivation under conditions which limit stem cell renewal but do not result in stem cell death or unidirectional differentiation into extraembryonic lineages such as extraembryonic endoderm. The method also facilitates the derivation of committed lineage progenitor cells which are no longer pluripotent but may give rise to mature somatic cells. Preferably the method provides for induction of somatic cells from embryonic stem cells.

In a further aspect of the invention, there is provided a method of producing large quantities of differentiated and undifferentiated cells.

In another aspect there is provided an undifferentiated cell line produced by the method of the present invention.

Preferably, the undifferentiated cell line is preserved by preservation methods such as cryopreservation. Preferably the method of cryopreservation is a method highly efficient for use with embryos such as vitrification. Most preferably, the method includes the Open Pulled Straw (OPS) vitrification method.

FIGURES

Figure 1:
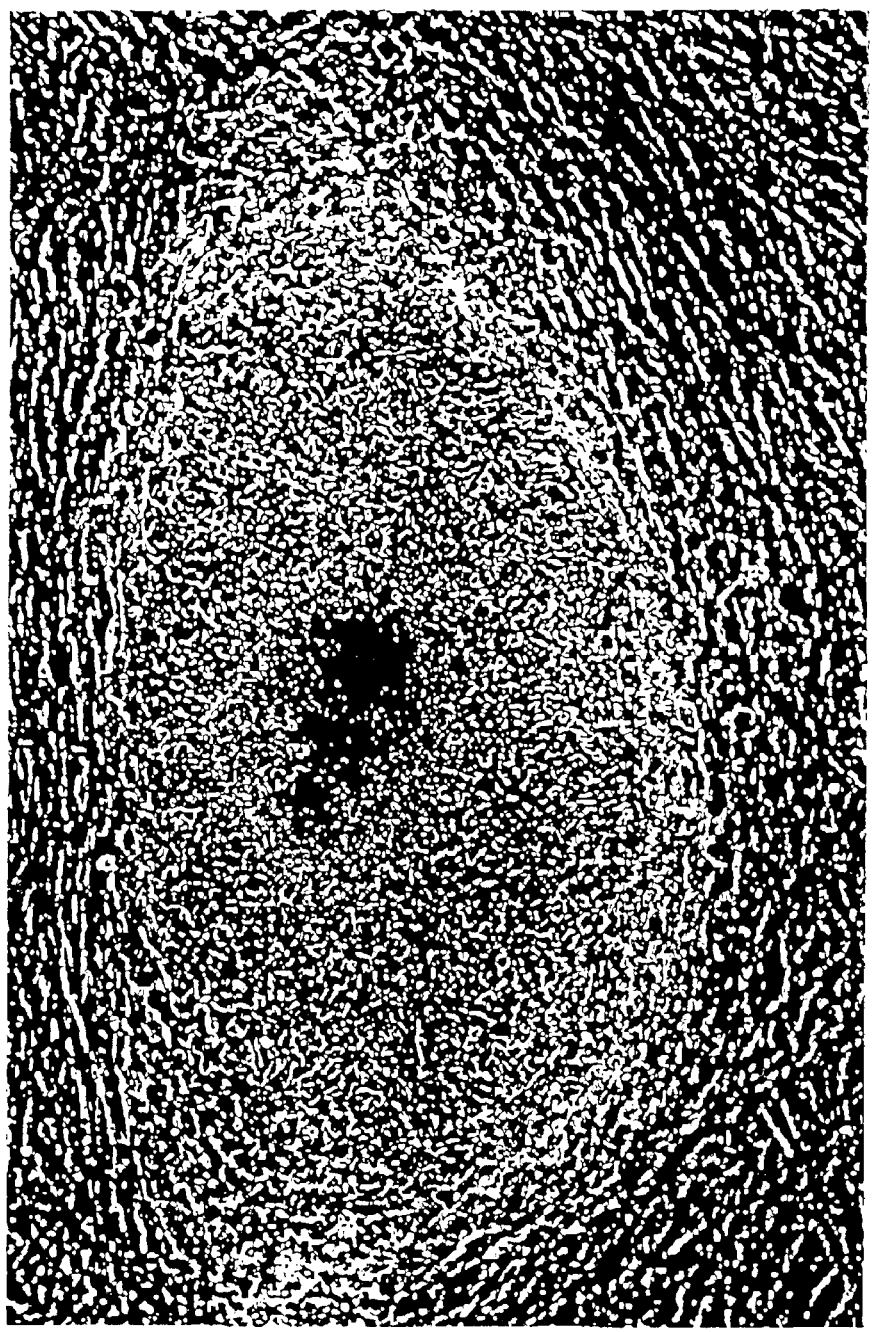
FIG. 1 shows a colony of undifferentiated human ES cell line HES-1.
Figure 2:
FIG. 2 shows a colony from the same cell line which has undergone differentiation.
Figure 3:
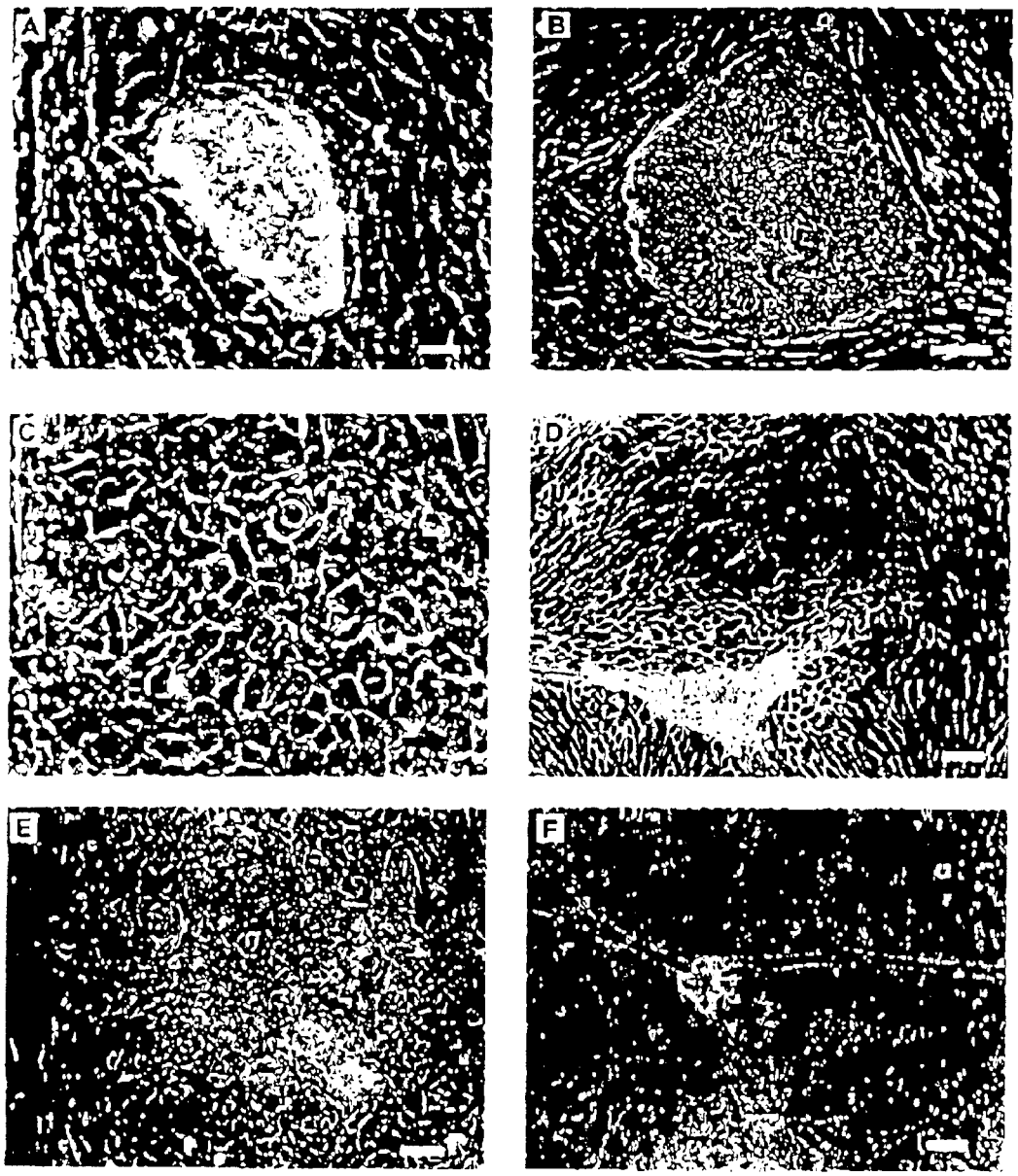

FIG. 3 shows phase contrast micrographs of ES cells and their differentiated progeny. A, inner cell mass three days after plating. B, colony of ES cells. C, higher magnification of an area of an ES cell colony. D, an area of an ES cell colony undergoing spontaneous differentiation during routine passage. E, a colony four days after plating in the absence of a feeder cell layer but in the presence of 2000 units/ml human LIF undergoing differentiation in its periphery. F, neuronal cells in a high density culture. Scale bars: A and C, 25 microns; B and E, 100 microns; D and F, 50 microns.

Figure 4:
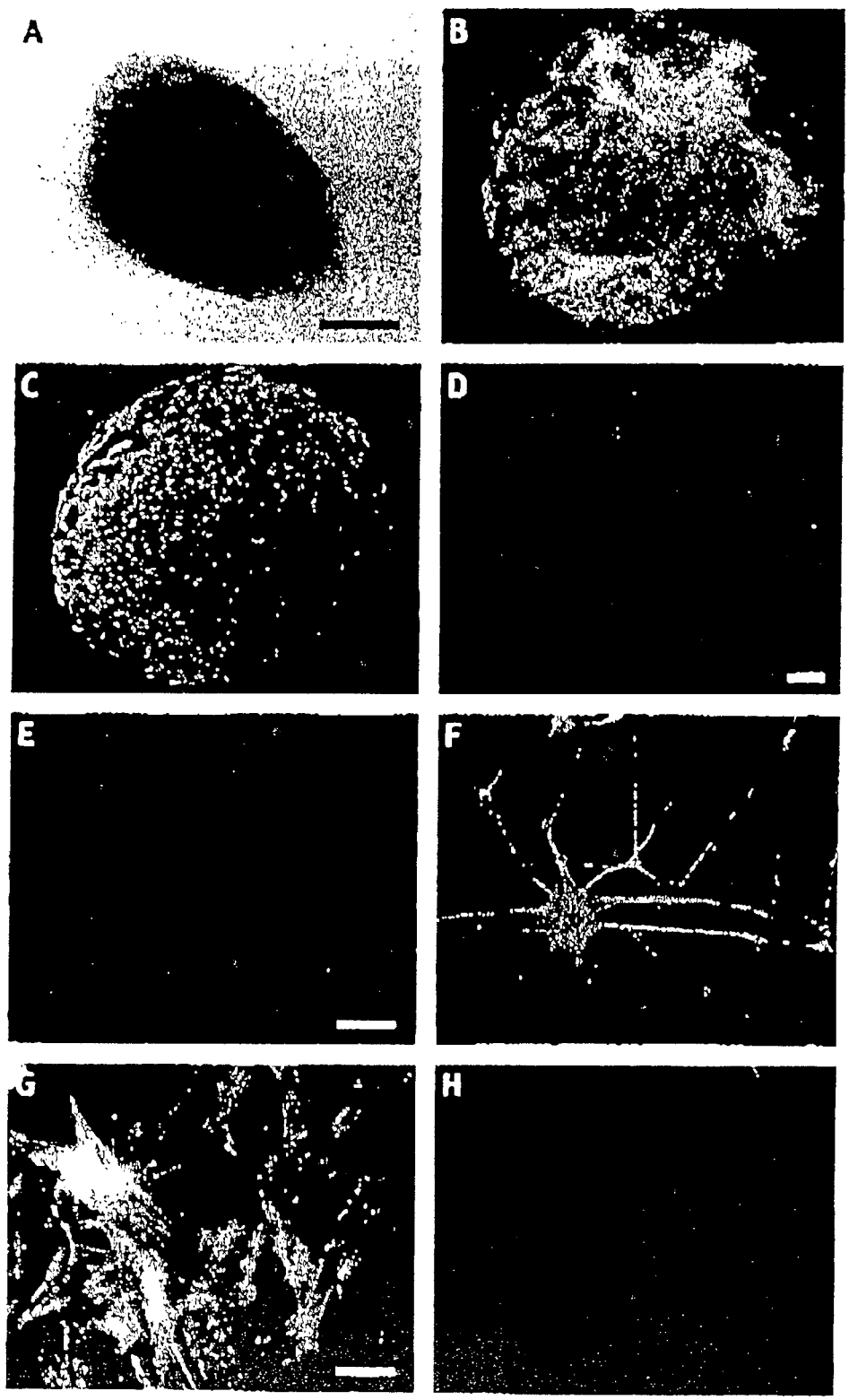

FIG. 4 shows marker expression in ES cells and their differentiated somatic progeny. A, ES cell colony showing histochemical staining for alkaline phosphatase. B, ES cell colony stained with antibody MC-813-70 recognising the SSEA-4 epitope. C, ES cell colony stained with antibody TRA1-60. D, ES cell colony stained with antibody GCTM-2. E, high density culture, cell body and processes of a cell stained with anti-neurofilament 68 kDa protein. F, high density culture, cluster of cells and network of processes emanating from them stained with antibody against neural cell adhesion molecule. G, high density culture, cells showing cytoplasmic filaments stained with antibody to muscle actin. H, high density culture, cell showing cytoplasmic filaments stained with antibody to desmin. Scale bars: A, 100 microns; B–D, and F, 200 microns; E, G and H, 50 microns.

Figure 5:
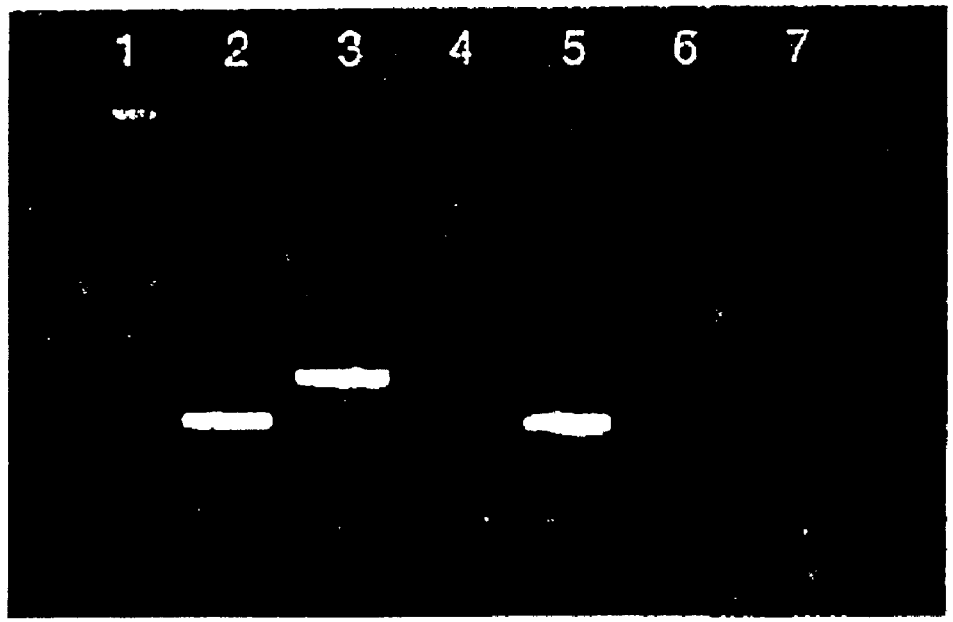

FIG. 5 shows RT-PCR analysis of the expression of Oct-4 and beta-actin in ES stem cells and high density cultures. 1.5% agarose gel stained with ethidium bromide. Lane 1, DNA markers. Lane 2, stem cell culture, beta actin. Lane 3, stem cell culture, Oct-4. Lane 4, stem cell culture, PCR for Oct-4 carried out with omission of reverse transcriptase. Lane 5, high density culture, beta actin. Lane 6, high density culture, Oct-4. Lane 7, high density culture, PCR for Oct-4 carried out with omission of reverse transcriptase. Beta actin band is 200 bp and Oct-4 band is 320 bp.

Figure 6:
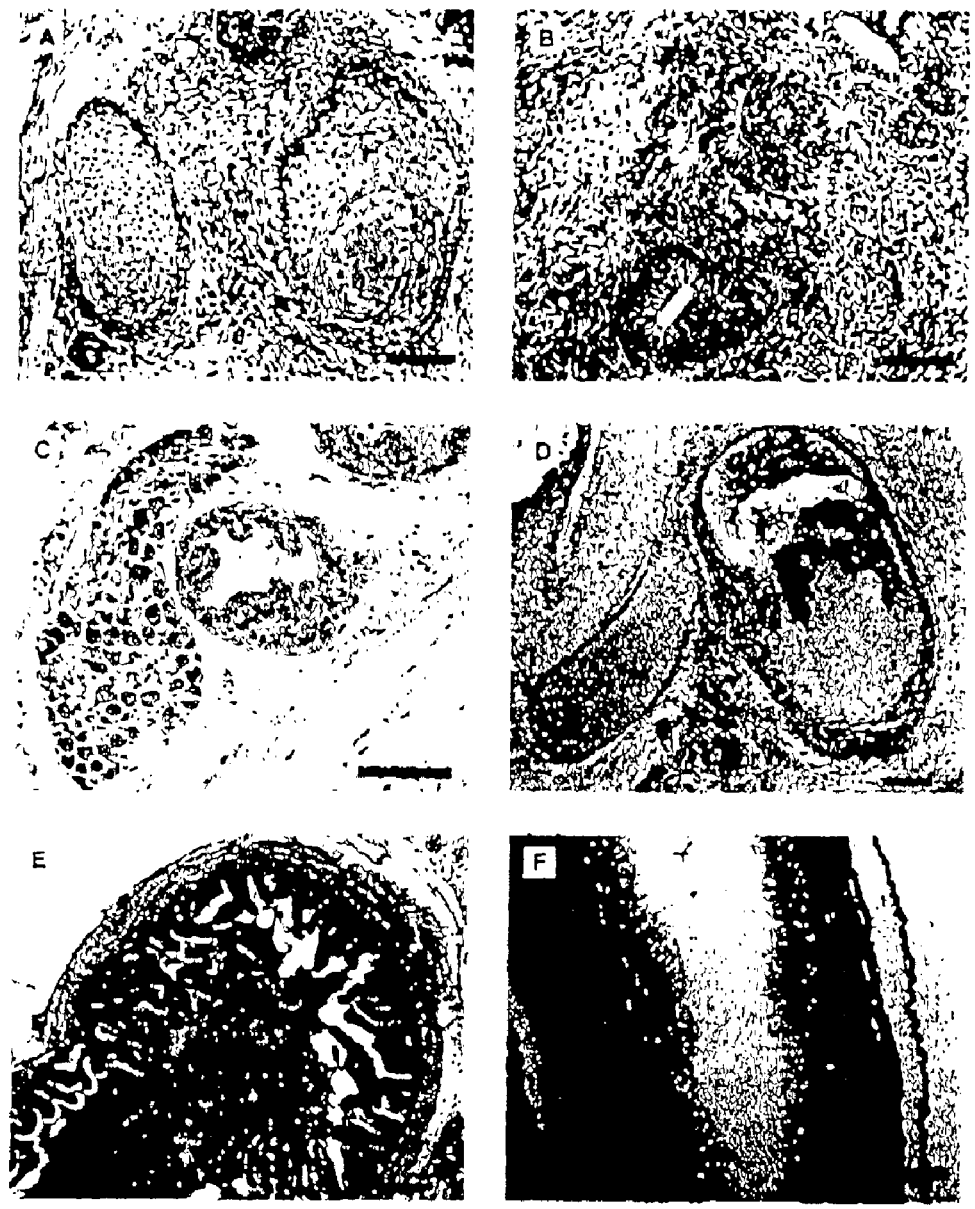

FIG. 6 shows histology of differentiated elements found in teratomas formed in the testis of SCID mice following inoculation of HES-1 or HES-2 colonies. A, cartilage and squamous epithelium, HES-2. B, neural rosettes, HES-2. C, ganglion, gland and striated muscle, HES-1. D, bone and cartilage, HES-1. E, glandular epithelium, HES-1. F, ciliated columnar epithelium, HES-1. Scale bars: A–E, 100 microns; F, 50 microns.

Figure 7:
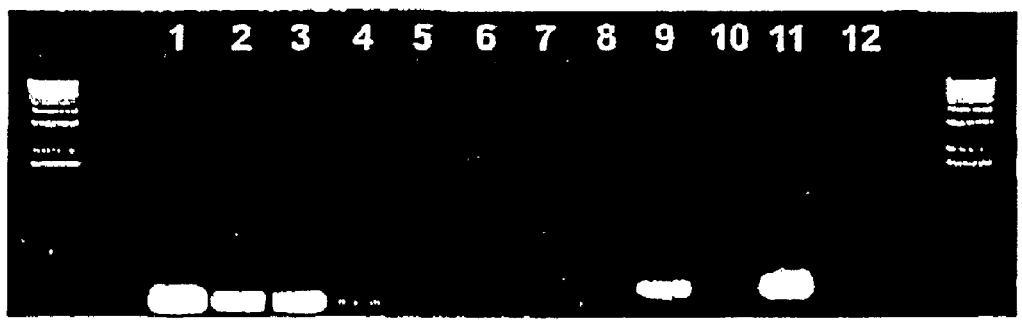

FIG. 7 shows RT-PCR analysis of the expression of the primitive neuroectodermal markers nestin and Pax-6 in neural precursor cells isolated from differentiating cultures. Lane 1 100 bp marker; lane 2 beta actin, HX 142 neuroblastoma positive control; lane 3 beta actin, neural progenitor sample one; lane 4 beta actin neural progenitor sample 2; lane 4 nestin HX 142; lane 5 nestin neural progenitor sample 1; lane 6 nestin but no RT, neural progenitor sample 2; lane 7 nestin, neural progenitor sample 2; lane 8, nestin but no RT, neural progenitor sample 2; lane 9 Pax-6 neural progenitor sample 1; lane 10 Pax-6 but no RT, neural progenitor sample 1; lane 11 Pax-6 neural progenitor sample 2; lane 12 Pax-6 but no RT, neural progenitor sample 2.

Figure 8:
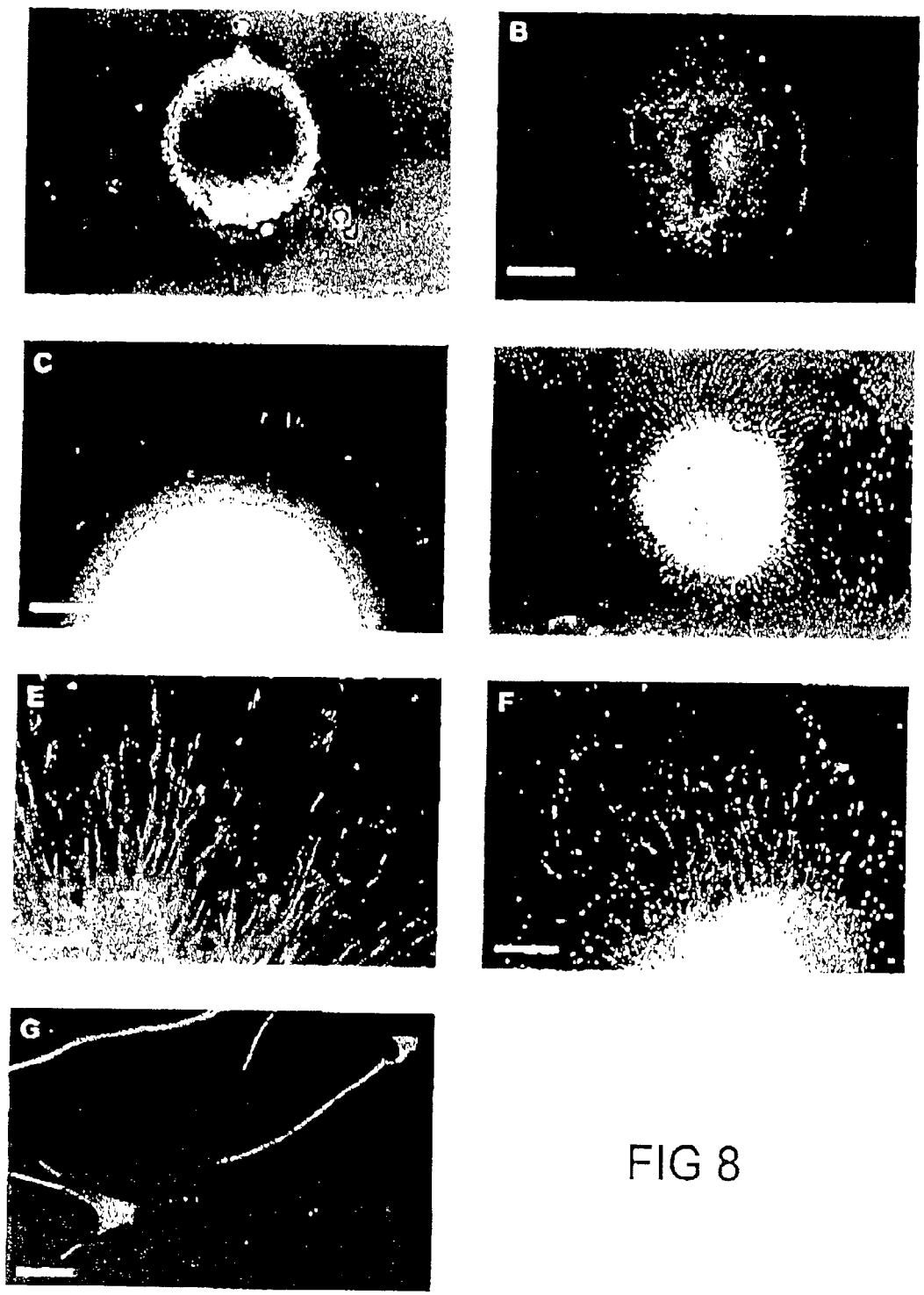

FIG. 8 shows phase contrast appearance of spheres of ES dervied neuronal progenitor cells and mature cells derived from them, and indirect immunofluorescence detection of markers characteristic of primitive neuroectoderm and mature neurons in these cells. A, phase contrast appearance of a spherical structure formed in serum-free medium after isolation of neural progenitor cells from a culture of differentiating ES cells; B, polysialyated N-CAM staining of such a sphere; C, Nestin staining of cells growing out onto the monolayer from a sphere; D, phase contrast morphology of an attached sphere with cells with elongated process emanating from it; E, structure similar to that in D stained with antibody to MAP-2ab; F, structure similar to that shown in D stained with antibody to neurofilament 160 kda protein; G, individual attached cells derived from a structure similar to that shown in D stained with beta-tubulin. Scale bar: A, 100 micron; B, 100 micron; C, 100 micron: D, 50 micron; E, 50 micron; F, 200 micron; G, 25 micron.

DETAILED DESCRIPTION OF THE INVENTION

In one aspect of the present invention there is provided a purified preparation of human undifferentiated embryonic stem cells capable of proliferation in vitro.

Proliferation in vitro may include cultivation of the cells for prolonged periods. The cells are substantially maintained in an undifferentiated state. Preferably the cells are maintained under conditions which do not induce cell death or extraembryonic differentiation.

Preferably, they are capable of maintaining an undifferentiated state when cultured on a fibroblast feeder layer preferably under non-differentiating conditions. Preferably the fibroblast feeder layer does not induce extraembryonic differentiation.

More preferably the cells have the potential to differentiate in vitro when subjected to differentiating conditions. Most preferably the cells have the capacity to differentiate in vitro into a wide array of somatic lineages.

The promotion of stem cells capable of being maintained in an undifferentiated state in vitro on one hand, and which are capable of differentiation in vitro into extraembryonic and somatic lineages on the other hand, allows for the study of the cellular and molecular biology of early human development, functional genomics, generation of differentiated cells from the stem cells for use in transplantation or drug screening and drug discovery in vitro.

Once the cells are maintained in the undifferentiated state, they may be differentiated to mature functional cells. The embryonic stem cells are derived from the embryo and are pluripotent and have the capability of developing into any organ or tissue type. Preferably the tissue type is selected from the group including blood cells, neuron cells or muscle cells.

In another aspect of the present invention there is provided an undifferentiated human embryonic stem cell wherein the cell is immunoreactive with markers for human pluripotent stem cells including SSEA-4, GCTM-2 antigen, TRA 1–60. Preferably, the cells express specific transcription factors such as Oct-4 as demonstrated by RT-PCR, or methods of analysis of differential gene expression, microarray analysis or related techniques. More preferably the cells maintain a diploid karyotype during prolonged cultivation in vitro.

Preferably, the stem cell will constitute a purified preparation of an undifferentiated stem cell line. More preferably, the stem cell line is a permanent cell line, distinguished by the characteristics identified above. They preferably have normal karyotype along with the characteristics identified above. This combination of defining properties will identify the cell lines of the invention regardless of the method used for their isolation.

Methods of identifying these characteristics may be by any method known to the skilled addressee. Methods such as (but not limited to) indirect immunoflourescence or immunocytochemical staining may be carried out on colonies of ES cells which are fixed by conventional fixation protocols then stained using antibodies against stem cell specific antibodies and visualised using secondary antibodies conjugated to fluorescent dyes or enzymes which can produce insoluble colored products. Alternatively, RNA may be isolated from the stem cells and RT-PCR or Northern blot analysis carried out to determine expression of stem cell specific genes such as Oct-4.

In a preferred embodiment the undifferentiated cells form tumours when injected in the testis of immunodeprived SCID mice these tumours include differentiated cells representative of all three germ layers. The germ layers are preferably endoderm, mesoderm and ectoderm. Preferably, once the tumours are established, they may be disassociated and specific differentiated cell types may be identified or selected by any methods available to the skilled addressee. For instance, lineage specific markers may be used through the use of fluorescent activated cell sorting (FACS) or other sorting method or by direct micro dissection of tissues of interest. These differentiated cells may be used in any manner. They may be cultivated in vitro to produce large numbers of differentiated cells which could be used for transplantation or for use in drug screening for example.

In another preferred embodiment, the undifferentiated cells differentiate in vitro to form somatic cells.

In another aspect, there is provided a somatic cell differentiated in vitro from an undifferentiated embryonic stem cell. There is also provided a committed progenitor cell capable of giving rise to mature somatic cells.

The cells may undergo differentiation in vitro to yield somatic cells as well as extrembryonic cells, such differentiation being characterised by novel gene expression characteristic of specific lineages as demonstrated by immunocytochemical or RNA analysis. Characterisation may be obtained by using expression of genes characteristic of pluripotent cells or particular lineages. Preferably, differential expression of Oct-4 may be used to identify stem cells from differentiated cells. Otherwise, the presence or absence of expression of other genes characteristic of pluripotent stem cells or other lineages may include Genesis, GDF-3 or Cripto. Analysis of these gene expressions may create a gene expression profile to define the molecular phenotype of an ES cell, a committed progenitor cell, or a mature differentiated cell of any type. Such analysis of specific gene expression in defined populations of cells from ES cultures is called cytomics. Methods of analysis of gene expression profiles include RT-PCR, methods of differential gene expression, microarray analysis or related techniques.

Differentiating cultures of the stem cells secrete HCG and AFP into culture medium, as determined by enzyme-linked immunosorbent assay carried out on culture supernatants. Hence this may also serve as a means of identifying the differentiated cells.

The differentiated cells forming somatic cells may also be characterised by expressed markers characteristic of differentiating cells. The in vitro differentiated cell culture may be differentiated into a single somatic cell type or it may differentiate into multiple somatic lineages. These multiple lineages may also be identified by detecting molecules such as neural cell adhesion molecule, neuro-filament proteins, desmin and smooth muscle action.

In a further aspect of the invention, there is provided a method of preparing undifferentiated human embryonic stem cells, said method including:

obtaining an in vitro fertilised human embryo and growing the embryo to a blastocyst stage of development;

removing inner cells mass (ICM) cells from the embryo;

culturing ICM cells under conditions which do not induce extraembryonic differentiation and cell death; and promote proliferation of undifferentiated stem cells; and recovering stem cells.

In a further preferred aspect of the present invention there is provided a method of preparing undifferentiated human embryonic stem cells, said method including:

obtaining an in vitro fertilised human embryo;

removing inner cells mass (ICM) cells from the embryo;

culturing ICM cells on a fibroblast feeder layer to obtain proliferation of embryonic stem cells; and recovering stem cells from the feeder layer.

Embryonic stem cells (ES) are derived from the embryo. These cells are undifferentiated and have the capability of differentiation to a variety of cell types. The "embryo" is defined as any stage after fertilization up to 8 weeks post conception. It develops from repeated division of cells and includes the stages of a blastocyst stage which comprises an outer trophectoderm and an inner cell mass (ICM).

The embryo required in the present method may be an in vitro fertilised embryo or it may be an embryo derived by transfer of a somatic cell nucleus into an enucleated oocyte of human or non human origin which is then activatd and allowed to develop to the blastocyst stage.

The embryo may be fertilised by any in vitro methods available. For instance, the embryo may be fertilised by using conventional insemination, or intracytoplasmic sperm injection. It is preferred that any embryo culture method is employed but it is most preferred that a method producing high quality (good morphological grade) blastocysts is employed. The high quality of the embryo can be assessed by morphological criteria. Most preferably the inner cell mass is well developed. These criteria can be assessed by the skilled addressee.

Following insemination, embryos may be cultured to the blastocyst stage. Embryo quality at this stage may be assessed to determine suitable embryos for deriving ICM cells. The embryos may be cultured in any medium that maintains their survival and enhances blastocyst development.

Preferably, the embryos are cultured in droplets under pre-equilibrated sterile mineral oil in IVF-50 or Scandinavian 1 (S1) or G1.2 medium (Scandinavian IVF). Preferably the incubation is for two days. If IVF-50 or S1 is used, on the third day, an appropriate medium such as a mixture of 1:1 of IVF-50 and Scandinavian-2 medium (Scandinavian IVF) may be used. From at least the fourth day, a suitable medium such as G2.2 or Scandinavian-2 (S2) medium may be used solely to grow the embryos to blastocyst stage (blastocysts). Preferably, only G2.2 medium is used from the fourth day onwards.

In a preferred embodiment, the blastocyst is subjected to enzymatic digestion to remove the zona pellucida or a portion thereof. Preferably the blastocyst is subjected to the digestion at an expanded blastocyst stage which may be approximately on day 6. Generally this is at approximately six days after insemination.

Any protein enzyme may be used to digest the zona pellucida or portion thereof from the blastocyst. Examples include pronase, acid Tyrodes solution, and mechanical methods such as laser dissection.

Preferably, Pronase is used. The pronase may be dissolved in PBS and G2 or S2 medium. Preferably the PBS and Scandinavian-2 medium is diluted 1:1. For digestion of zone pellucida from the blastocyst, approximately 10 units/ml of Pronase may be used for a period sufficient to remove the zona pellucida. Preferably approximately 1 to 2 mins, more preferably 1–1.5 mins is used.

The embryo (expanded blastocyst) may be washed in G2.2 or S2 medium, and further incubated to dissolve the zona pellucida. Preferably, further digestion steps may be used to completely dissolve the zona. More preferably the embryos are further incubated in pronase solution for 15 seconds. Removal of he zona pellucida thereby exposes the trophectoderm.

In a preferred aspect of the invention the method further includes the following steps to obtain the inner cell mass cell, said steps including:

treating the embryo to dislodge the trophectoderm of the embryo or a portion thereof;

washing the embryo with a G2.2 or S2 medium to dislodge the trophectoderm or a portion thereof; and obtaining inner cell mass cells of the embryo.

Having had removed the zona pellucida, the ICM and trophectoderm become accessible. Preferably the trophectoderm is separated from the ICM. Any method may be employed to separate the trophectoderm from the ICM. Preferably the embryo (or blastocyst devoid of zona pellucida) is subjected to immuno-surgery. Preferably it is treated with an antibody or antiserum reactive with epitopes on the surface of the trophectoderm. More preferably, the treatment of the embryo, (preferably an embryo at the blastocyst stage devoid of zona pellucida) is combined with treatment with complement. The antibody and/or antiserum and complement treatment may be used separately or together. Preferred combinations of antibody and/or antiserum and complement include anti-placental alkaline phosphatase antibody and Baby Rabbit complement (Serotec) or anti-human serum antibody (Sigma) combined with Guinea Pig complement (Gibco).

Preferably the antibodies and complement are diluted in G2.2 or S2 medium. The antibodies and complement, excluding anti-placental alkaline phosphate (anti-AP) are diluted 1:5 whereas anti-AP antibody is diluted 1:20 with S-2 medium.

Preferably the embryo or blastocyst (preferably having the zona pellucida removed) is subjected to the antibody before it is subjected to the complement. Preferably, the embryo or blastocyst is cultured in the antibody for a period of approximately 30 mins.

Following the antibody exposure, it is preferred that the embryo is washed. Preferably it is washed in G2.2 or S2 medium. The embryo or blastocyst preferably is then subjected to complement, preferably for a period of approximately 30 mins.

G2.2 or S2 (Scandinavian-2) medium is preferably used to wash the embryo or blastocyst to dislodge the trophectoderm or a portion thereof. Dislodgment may be by mechanical means. Preferably the dislodgment is by pipetting the blastocyst through a small bore pipette.

The ICM cells may then be exposed and ready for removal and culturing. Culturing of the ICM cells is conducted on a fibroblast feeder layer. In the absence of a fibroblast feeder layer, the cells will differentiate. Leukaemia inhibitory factor (LIF) has been shown to replace the feeder layer in some cases and maintain the cells in an undifferentiated state. However, this seems to only work for mouse cells. For human cells, high concentration of LIF were unable to maintain the cells in an undifferentiated state in the absence of a fibroblast feeder layer.

The conditions which do not induce extraembryonic differentiation and cell death may include cultivating the embryonic stem cells on a fibroblast feeder layer which does not induce extraembryonic differentiation and cell death.

Mouse or human fibroblasts are preferably used. They may be used separately or in combination. Human fibroblasts provide support for stem cells, but they create a non-even and sometimes non-stable feeder layer. However, they may combine effectively with mouse fibroblasts to obtain an optimal stem cell growth and inhibition of differentiation.

The cell density of the fibroblast layer affects its stability and performance. A density of approximately 25,000 human and 70,000 mouse cells per cm$^2$ is most preferred. Mouse fibroblasts alone are used at 75,000–100,000/cm$^2$. The feeder layers are preferably established 6–48 hours prior to addition of ES cells.

Preferably the mouse or human fibroblast cells are low passage number cells. The quality of the fibroblast cells affects their ability to support the stem cells. Embryonic fibroblasts are preferred. For mouse cells, they may be obtained from 13.5 day old foetuses. Human fibroblasts may be derived from embryonic or foetal tissue from termination of pregnancy and may be cultivated using standard protocols of cell culture.

The guidelines for handling the mouse embryonic fibroblasts may include minimising the use of trypsin digestion and avoidance of overcrowding in the culture. Embryonic fibroblasts that are not handled accordingly will fail to support the growth of undifferentiated ES cells. Each batch of newly derived mouse embryonic fibroblasts is tested to confirm its suitability for support and maintenance of stem cells.

Fresh primary embryonic fibroblasts are preferred in supporting stem cell renewal as compared to frozen-thawed fibroblasts. Nevertheless, some batches will retain their supportive potential after repeated freezing and thawing. Therefore each fresh batch that has proved efficient in supporting ES cells renewal is retested after freezing and thawing. Batches that retain their potential after freezing and thawing are most preferably used.

Some mouse strains yield embryonic fibroblasts which are more suitable for stem cell maintenance than those of other strains. For example, fibroblasts derived from inbred 129/Sv or CBA mice or mice from a cross of 129/Sv with C57/B16 strains have proven highly suitable for stem cell maintenance.

Isolated ICM masses may be plated and grown in culture conditions suitable for human stem cells.

It is preferred that the feeder cells are treated to arrest their growth. Several methods are available. It is preferred that they are irradiated or are treated with chemicals such as mitomycin C which arrests their growth. Most preferably, the fibroblast feeder cells are treated with mitomycin C (Sigma).

The fibroblast feeder layer maybe generally plated on a gelatin treated dish. Preferably, the tissue culture dish is treated with 0.1% gelatin.

The fibroblast feeder layer may also contain modified fibroblasts. For instance, fibroblasts expressing recombinant membrane bound factors essential for stem cell renewal may be used. Such factors may include for example human multipotent stem cell factor.

Inner cell mass cells may be cultured on the fibroblast feeder layer and maintained in an ES medium. A suitable medium is DMEM (GIBCO, without sodium pyruvate, with glucose 4500 mg/L) supplemented with 20% FBS (Hyclone, Utah), (betamercaptoethanol—0.1 mM (GIBCO), non essential amino acids—NEAA 1% (GIBCO), glutamine 2 mM. (GIBCO), and penicillin 50 $\mu$p/ml, streptomycin 50 $\mu$g/ml (GIBCO). In the early stages of ES cell cultivation, the medium maybe supplemented with human recombinant leukemia inhibitory factor hLIF preferably at 2000 $\mu$p/ml. However, LIF generally is not necessary. Any medium may be used that can support the ES cells, The ES medium may be further supplemented with soluble growth factors which promote stem cell growth or survival or inhibit stem cell differentiation. Examples of such factors include human multipotent stem cell factor, or embryonic stem cell renewal factor.

The isolated ICM may be cultured for at least six days. At this stage, a colony of cells develops. This colony is comprised principally of undifferentiated stem cells. They may exist on top of differentiated cells. Isolation of the undifferentiated cells may be achieved by chemical or mechanical means or both. Preferably mechanical isolation and removal by a micropipette is used. Mechanical isolation may be combined with a chemical or enzymatic treatment to aid with dissociation of the cells, such as $Ca^{2+}/Mg^{2+}$ free PBS medium or dispase.

In a further aspect of the invention, the method further includes:
  replating the stem cells from the fibroblast feeder layer onto another fibroblast feeder layer; and
  culturing the stem cells for a period sufficient to obtain proliferation of morphologically undifferentiated stem cells.

A further replating of the undifferentiated stem cells is performed. The isolated clumps of cells from the first fibroblast feeder layer may be replated on fresh human/mouse fibroblast feeder layer in the same medium as described above.

Preferably, the cells are cultured for a period of 7–14 days. After this period, colonies of undifferentiated stem cells may be observed. The stem cells may be morphologically identified preferably by the high nuclear/cytoplasmic ratios, prominent nucleoli and compact colony formation. The cell borders are often distinct and the colonies are often flatter than mouse ES cells. The colonies resemble those formed by pluripotent human embryonal carcinoma cell lines such as GCT 27 X-1.

In an even further aspect of the invention, the method further includes propagating the undifferentiated stem cells. The methods of propagation may initially involve removing clumps of undifferentiated stem cells from colonies of cells. The dispersion is preferably by chemical or mechanical means or both. More preferably, the cells are washed in a $Ca^{2+}/Mg^{2+}$ free PBS or they are mechanically severed from the colonies or a combination of the two methods. In both methods, cells may be propagated as clumps of about 100 cells about every 7 days.

In the first method, $Ca^{2+}/Mg^{2+}$ free PBS medium may be used to reduce cell-cell attachments. Following about 15–20 minutes, cells gradually start to dissociate from the monolayer and from each other and desired size clumps can be isolated. When cell dissociation is partial, mechanical dissociation using the sharp edge of the pipette may assist with cutting and the isolation of the clumps.

An alternative chemical method may include the use of an enzyme. The enzyme may be used alone or in combination with a mechanical method. Preferably, the enzyme is dispase.

An alternative approach includes the combined use of mechanical cutting of the colonies followed by isolation of the subcolonies by dispase. Cutting of the colonies may be performed in PBS containing $Ca^{2+}$ and $Mg^{2+}$. The sharp edge of a micropipette may be used to cut the colonies to clumps of about 100 cells. The pipette may be used to scrape and remove areas of the colonies. The PBS is preferably changed to regular equilibrated human stem cell medium containing dispase (Gibco) 10 mg/ml and incubated for approximately 5 minutes at 37° C. in a humidified atmosphere containing 5% $CO_2$. As soon as the clumps detached they may be picked up by a wide bore micro-pipette, washed in PBS containing $Ca^{2+}$ and $Mg^{2+}$ and transferred to a fresh fibroblast feeder layer.

The fibroblast feeder layer may be as described above.

Undifferentiated embryonic stem cells have a characteristic morphology as described above. Other means of identifying the stem cells may be by cell markers or by measuring expression of genes characteristic of pluripotent cells.

Examples of genes characteristic of pluripotent cells or particular lineages may include (but are not limited to) Oct-4 and Pax-6 or nestin as markers of stem cells and neuronal precursors respectively. Other genes characteristic of stem cells may include Genesis, GDF-3 and Cripto. Such gene expression profiles may be attained by any method including RT-PCR, methods of differential gene expression, microarray analysis or related techniques.

Preferably the stem cells may be identified by being immunoreactive with markers for human pluripotent stem cells including SSEA-4, GCTM-2 antigen, TRA 1–60. Preferably the cells express the transcription factor Oct-4. The cells also maintain a diploid karyotype.

The stem cells may be further modified at any stage of isolation. They may be genetically modified through introduction of vectors expressing a selectable marker under the control of a stem cell specific promoter such as Oct-4. Some differentiated progeny of embryonic stem cells may produce products which are inhibitory to stem cell renewal or survival. Therefore selection against such differentiated cells, facilitated by the introduction of a construct such as that described above, may promote stem cell growth and prevent differentiation.

The stem cells may be genetically modified at any stage with markers so that the markers are carried through to any stage of cultivation. The markers may be used to purify the differentiated or undifferentiated stem cell population at any stage of cultivation.

Progress of the stem cells and their maintenance in a differentiated or undifferentiated stage may be monitored in a quantitative fashion by the measurement of stem cell specific secreted products into the culture medium or in fixed preparations of the cells using ELISA or related techniques. Such stem cell specific products might include the soluble form of the CD30 antigen or the GCTM-2 antigen or they may be monitored as described above using cell markers or gene expression.

In another aspect of the invention there is provided a method of induction of differentiation of stem cells in vitro.

The undifferentiated cell lines of the present invention may be cultured indefinitely until a differentiating signal is given.

In the presence of a differentiation signal, undifferentiated ES cells in the right conditions will differentiate into derviatives of the embryonic germ layers (endoderm, mesoderm and ectoderm), and/or extraembryonic tissues. This differentiation process can be controlled.

Conditions for obtaining differentiated cultures of somatic cells from embryonic stem cells are those which are non-permissive for stem cell renewal, but do not kill stem cells or drive them to differentiate exclusively into extraembryonic lineages. A gradual withdrawal from optimal conditions for stem cell growth favours somatic differentiation. The stem cells are initially in an undifferentiated state and can be induced to differentiate. Generally the presence of a fibroblast feeder layer will maintain these cells in an undifferentiated state. This has been found to be the case with the cultivation of mouse and human ES cells. However, without being restricted by theory, it has now become evident that the type and handling of the fibroblast feeder layer is important for maintaining the cells in an undifferentiated state or inducing differentiation of the stem cells.

Somatic differentiation in vitro of the ES cell lines is a function of the period of cultivation following subculture, the density of the culture, and the fibroblast feeder cell layer. It has been found that somatic differentiation is morphologically apparent and demonstrable by immunochemistry approximately 14 days following routine subcultivation as described above in areas of the colony which are remote from direct contact with the feeder cell layer (in contrast to areas adjacent to the feeder cell layer where rapid stem cell growth is occuring such as the periphery of a colony at earlier time points after subcultivation), or in cultures which have reached confluence. Depending upon the method of preparation and handling of the mouse embryo fibroblasts, the mouse strain from which the fibroblasts are derived, and the quality of a particular batch, stem cell renewal, extraembryonic differentiation or somatic differentiation may be favoured.

As previously mentioned the guidelines for handling the mouse embryonic fibroblasts include minimising the use of trypsin digestion during passage and avoidance of over crowded cultures. Mouse embryonic fibroblasts which are not handled accordingly will induce the differentiation of human ES cells mainly into extraembryonic lineages.

Each batch of freshly prepared primary embryonic fibroblasts is routinely tested to determine its suitability for the support of stem cell renewal, the induction of somatic differentiation or the induction of extraembryonic differentiation.

Fresh primary embryonic fibroblasts are preferred in supporting stem cell renewal and/or induction of somatic differentiation as compared to frozen-thawed fibroblasts. Nevertheless, some batches will retain their supportive potential after repeated freezing and thawing. Therefore each fresh batch that has proved efficient in supporting ES cells renewal and/or induction of somatic differentiation is retested after freezing and thawing. Batches that retain their potential after freezing and thawing are most preferably used.

Any mouse strain may be used although crosses between the strains 129/Sv and C57/BL6 or inbred 129/Sv or CBA mouse are more preferably used.

Once a suitable fibroblast cell line is selected, it may be used as a differentiation inducing fibroblast feeder layer to induce the undifferentiated stem cells to differentiate into a somatic lineage or multiple somatic lineages. These may be identified using markers or gene expression as described above. Preferably the fibroblast feeder layer does not induce extraembryonic differentiation and cell death.

The modulation of stem cell growth by appropriate use of fibroblast feeder layer and manipulation of the culture conditions thus provides an example whereby somatic differentiation may be induced in-vitro concomitant with the limitation of stem cell renewal without the induction of widespread cell death or extraembryonic differentiation.

Other manipulations of the culture conditions may be used to arrest stem cell renewal without causing stem cell death or unidirectional extraembryonic differentiation, thereby favouring differentiation of somatic cells.

Differentiation may also be induced by cultivating to a high density in monolayer or on semi-permeable membranes so as to create structures mimicing the postimplantation phase of human development, or any modification of this approach. Cultivation in the presence of cell types representative of those known to modulate growth and differentiation in the vertebrate embryo (eg. endoderm cells or cells derived from normal embyronic or neoplastic tissue) or in adult tissues (eg. bone marrow stromal preparation) may also induce differentiation, modulate differentiation or induce maturation of cells within specific cell lineage so as to favour the establishment of particular cell lineages.

Chemical differentiation may also be used to induce differentiation. Propagation in the presence of soluble or membrane bound factors known to modulate differentiation of vertebrate embryonic cells, such as bone morphogenetic protein-2 or antagonists of such factors, may be used.

Applicants have found that Oct-4 is expressed in stem cells and down-regulated during differentiation and this strongly indicates that stem cell selection using drug resistance genes driven by the Oct-4 promoter will be a useful avenue for manipulating human ES cells. Directed differentiation using growth factors, or the complementary strategy of lineage selection coupled with growth factor enhancement could enable the selection of populations of pure committed progenitor cells from spontaneously differentiating cells generated as described here.

Genetic modification of the stem cells or further modification of those genetically modified stem cells described above may be employed to control the induction of differentiation. Genetic modification of the stem cells so as to introduce a construct containing a selectable marker under the control of a promoter expressed only in specific cell lineages, followed by treatment of the cells as described above and the subsequent selection for cells in which that promoter is active may be used.

In another aspect of the invention, there are provided both committed progenitor cells capable of self renewal or differentiation into one or limited number of somatic cell lineages, as well as mature differentiated cell produced by the methods of the present invention.

Once the cells have been induced to differentiate, the various cell types, identified by means described above, may be separated and selectively cultivated.

Selective cultivation means isolation of specific lineages of progenitors or mature differentiated cells from mixed populations preferably appearing under conditions unfavourable for stem cell growth and subsequent propagation of these specific lineages. Selective cultivation may be used to isolate populations of mature cells or populations of lineage specific committed progenitor cells. Isolation may be achieved by various techniques in cell biology including the following alone or in combination: microdissection; immunological selection by labelling with antibodies against epitopes expressed by specific lineages of differentiated cells followed by direct isolation under flourescence microscopy, panning, immunomagnetic selection, or selection by flow cytometry; selective conditions favouring the growth or adhesion of specific cell lineages such as exposure to particular growth or extracellular matrix factors or selective cell-cell adhesion; separation on the basis of biophysical properties of the cells such as density; disaggregation of mixed populations of cells followed by isolation and cultivation of small clumps of cells or single cells in separate culture vessels and selection on the basis of morphology, secretion of marker proteins, antigen expression, growth properties, or gene expression; lineage selection using lineage specific promoter constructs driving selectable markers or other reporters.

For example areas of cells which are destined to give rise to clusters of neuronal cells as shown in FIG. 3F may be identified in high density cultures by characteristic morphological features identified under phase contrast or stereo microscopy. These areas of calls may be isolated and replated in serum-free medium, whereupon they form spherical structures, Cells in these spheres initially express markers of primitive neuroectoderm, such as the intermediate filament protein nestin and the transcription factor Pax-6. When plated on an appropriate substrate, differentiated cells grow out as a monolayer from these precursors and acquire morphology and expression of markers such as the 160 kd neurofilament protein and Map-2AB which are characteristic of mature neurons. These observations on cells of the neuronal lineage establish the principle that both committed progenitor cells and fully differentiated cells may be isolated and characterised from embryonic stem cell cultures using the techniques described.

In another aspect there is provided an undifferentiated cell line produced by the method of the present invention.

Specific cell lines HES-1 and HES-2 were isolated by the procedures described above and have the properties described above.

In another aspect of the invention there is provided a cell composition including a human differentiated or undifferentiated cell preferably produced by the method of the present invention, and a carrier.

The carrier may be any physiologically acceptable carrier that maintains the cells. It may be PBS or ES medium.

The differentiated or undifferentiated cells may be preserved or maintained by any methods suitable for storage of biological material. Vitrification of the biological material is the preferred method over the traditional slow-rate freezing methods.

Effective preservation of ES cells is highly important as it allows for continued storage of the cells for multiple future usage. Although traditional slow freezing methods, commonly utilised for the cryo-preservation of cell lines, may be used to cryo-preserve undifferentiated or differentiated cells, the efficiency of recovery of viable human undifferentiated ES cells with such methods is extremely low. ES cell lines differ from other cell lines since the pluripotent cells are derived from the blastocyst and retain their embryonic properties in culture. Therefore, cryo-preservation using a method which is efficient for embryos is most appropriate. Any method which is efficient for cryo-preservation of embryos may be used. Preferably, vitrification method is used. More preferably the Open Pulled Straw (OPS) vitrification method previously described by Vajta, G. et al (1998) Molecular Reproduction and Development, 51, 53–58, is used for cryopreserving the undifferentiated cells. More preferably, the method described by Vajta, G. et al (1998) Cryo-Letters, 19, 389–392 is employed. Generally, this method has only been used for cryopreserving embryos.

The differentiated or undifferentiated cells may be used as a source for isolation or identification of novel gene products including but not limited to growth factors, differentiation factors or factors controlling tissue regeneration, or they may be used for the generation of antibodies against novel epitopes. The cell lines may also be used for the development of means to diagnose, prevent or treat congenital diseases.

Much attention recently has been devoted to the potential applications of stem cells in biology and medicine. The properties of pluripotentiality and immortality are unique to ES cells and enable investigators to approach many issues in human biology and medicine for the first time. ES cells potentially can address the shortage of donor tissue for use in transplantation procedures, particularly where no alternative culture system can support growth of the required committed stem cell. ES cells have many other far reaching applications in human medicine, in areas such as embryological research, functional genomics, identification of novel growth factors, and drug discovery, and toxicology.

The present invention will now be more fully described with reference to the following examples. It should be understood, however, that the description following is illustrative only and should not be taken in any way as a restriction on the generality of the invention described above.

REFERENCES

Evans, M. J. and Kaufman, M. Establishment in culture of pluripotential stem cells from mouse embryos. *Nature* 292, 151–156 (1981).

Martin, G. R. Isolation of a pluripotent cell line from early mouse embryos cultured in medium conditioned by teratocarcinoma stem cells. *Proc. Natl. Acad. Sci U.S.A.* 78, 7634–7638 (1981).

Andrews, P. W. et al. Pluripotent embryonal carcinoma clones derived from the human teratocarcinoma cell line Tera-2. *Lab. Invest.* 50, 147–162 (1984).

Pera, M. F., Cooper, S., Mills, J., & Parrington, J. M. Isolation and characterization of a multipotent clone of human embryonal carcinoma-cells. *Differentiation* 42, 10–23 (1989).

Thomson, J. A. et al. Isolation of a primate embryonic stem cell line. *Proc. Natl. Acad. Sci. U.S.A.* 92, 7844–7844 (1995).

Thomson, J. A. et al. Pluripotent cell lines derived from common marmoset (*Callithrix jacchus*) blastocysts. *Biol. Reprod.* 55, 254–259. (1996).

Bongso A., Fong C. Y., Ng S. C., and Ratnam, S. Isolation and culture of inner cell mass cells from human blastocysts. *Hum. Reprod.* 9, 2110–2117 (1994).

Thomson, J. A. et al. Embryonic stem cell lines derived from human blastocysts. *Science* 282, 1145–1147 (1998).

Andrews, P. W. et al. Comparative-analysis of cell-surface antigens expressed by cell-lines derived from human germ-cell tumors. *Int. J. Cancer* 66, 806–816 (1996).

Cooper, S., Pera, M. F., Bennett, W., & Finch, J. T. A novel keratan sulfate proteoglycan from a human embryonal carcinoma cell-line. *Biochem. J.* 286, 959–966 (1992).

Pera, M. F. et al. Analysis of cell-differentiation lineage in human teratomas using new monoclonal-antibodies to cytostructural antigens of embryonal carcinoma-cells. *Differentiation* 39, 139–149 (1988).

Fong C. Y., and Bongso A. Comparison of human blastulation rates and total cell number in sequential culture media with and without co-culture. *Hum. Reprod.* 14, 774–781 (1999).

Fong C. Y. et al. Ongoing pregnancy after transfer of zona-free blastocysts: implications for embryo transfer in the human. *Hum. Reprod.* 12, 557–560 (1997).

Solter D., and Knowles, B. Immunosurgery of mouse blastocyst. *Proc. Natl. Acad. Sci. U.S.A.* 72, 5099–5102 (1975).

Vajta G, Holm P, Kuwayama M, Both P J, Jacobsen H, Greve T, Callesen H. Open pulled straw (OPS) vitrification: A new way to reduce cryoinjuries of bovine ova and embryos. Molecular Reproduction and Development 1998, 51: 53–58.

Vajta G, Lewis I M, Kuwayama M, Greve T, Callesen H. Sterile application of the opened pulled straw (OPS) vitrification method. Cryo-Letters 1998, 19: 389–392.

EXPERIMENTAL PROTOCOLS

1. Derivation and propagation of ES cells.

Fertilised oocytes were cultured to the blastocyst stage (day 6 after insemination), in sequential media, according to a standard co-culture free protocol (Fong C. Y., and Bongso A. Comparison of human blastulation rates and total cell number in sequential culture media with and without co-culture. *Hum. Reprod.* 14, 774–781 (1999)). After zona pellucida digestion by pronase (Sigma, St. Louis, Mo.)(Fong C. Y. et al. Ongoing pregnancy after transfer of zona-free blastocysts: implications for embryo transfer in the human. *Hum. Reprod.* 12, 557–560 (1997)), ICM were isolated by immunosurgery (Solter D., and Knowles, B. Immunosurgery of mouse blastocyst. *Proc. Natl. Acad. Sci. U.S.A.* 72, 5099–5102 (1975)) using anti-human serum antibody (Sigma) followed by exposure to guinea pig complement (Life Technologies, Gaithersburg, Md.). ICM were then cultured on mitomycin C mitotically inactivated mouse embryonic fibroblast feeder layer (75,000 cells/cm2) in gelatine coated tissue culture dishes. The culture medium consisted of DMEM (Gibco, without sodium pyruvate, glucose 4500 mg/L) supplemented with 20% fetal bovine serum (Hyclone, Logan, Utah), 0.1 mM beta-mercaptoethanol, 1% non essential amino acids, 2 mM glutamine, 50 $\mu$/ml penicillin and 50 $\mu$g/ml streptomycin (Life Technologies). During the isolation and early stages of ES cell cultivation, the medium was supplemented with human recombinant leukemia inhibitory factor hLIF at 2000 $\mu$/ml (Amrad, Melbourne, Australia). 6–8 days after initial plating, ICM like clumps were removed mechanically by a micropipette from differentiated cell outgrowths and replated on fresh feeder layer. The resulting colonies were further propagated in clumps of about 100 stem cell like cells, on mouse feeder layer, about every 7 days. The clumps were either dissociated mechanically, or with a combined approach of mechanical slicing followed by exposure to dispase (10 mg/ml, Life Technologies).

(a) Embryo culture

Following insemination, embryos were cultured in droplets under pre-equilibrated sterile mineral oil in IVF-50 medium (Scandinavian 2 medium) for 2 days.

A mixture 1:1 of IVF-50 and Scandinavian 2 medium (Scandinavian 2 medium) was used in the third day.

From the forth day of culture, only Scandinavian 2 medium was used to grow the cleavage stage embryos to blastocysts.

(b) Zona pellucida digestion.

Zona pellucida digestion was performed at the expanded blastocyst stage on day 6.

The digestion solution included Pronase (Sigma, TC tested) 10 u in PBS and Scandinavian 2 medium (1:1).

The embryos were incubated in pronase solution for 1–1.5 min. washed in Scandinavian 2 medium and incubated for 30 minutes. If the zona was not completely dissolved, the embryos were further incubated in pronase solution for 15 seconds.

(c) Human stem cell culture.

Human stem cells were grown on MMC treated fibroblasts' feeder layer. Fibroblasts were plated on gelatine treated dishes. A combination of human and mouse derived fibroblasts were used at a density of approximately 25,000 and 70,000 cells per cm$^2$ respectively. The fibroblasts were plated up to 48 hours before culture of the stem cells. Mouse fibroblasts only could also support the growth of the stem cells. However, while human fibroblasts could also support stem cells, they created an uneven and unstable feeder layer. Therefore, the human fibroblasts were combined with the mouse fibroblasts to augment and achieve better support of growth and prevention of differentiation.

The medium that was used for the growth of human stem was DMEM (GIBCO, without sodium pyruvate, with glucose 4500 mg/L) supplemented with 20% FBS (Hyclone, Utah) $\beta$-mercaptoethanol-0.1 mM (GIBCO), Non Essential Amino Acids—NEAA 1% (GIBCO), glutamine 2 mM. (GIBCO), penicillin 50 u/ml, and streptomycin 50 $\mu$g/ml (GIBCO). At the initial isolation of the stem cells the medium was supplemented by hLIF 2000 u/ml. It was later shown that LIF was not necessary.

(d) Human stem cell propagation:

Following plating, the isolated ICM attached and was cultured for 6 days. At that stage, a colony which included a clump of stem cells on top of differentiated cells developed. The ICM clump was isolated and removed mechanically by a micro-pipette with the aid of using Ca/Mg free PBS medium to reduce cell to cell attachments.

The isolated clump was replated on fresh human/mouse fibroblast feeder layer. Following 2 weeks of culture, a colony with typical morphology of primate pluripotent stem cells developed. The stem cells were further propagated in one of two methods. In both methods cells which appeared nondifferentiated were propagated in clumps of about 100 cells every 5–7 days.

In the first method, Ca/Mg free PBS medium was used to reduce cell to cell attachments. Following about 15–20 minutes, cells gradually start to dissociate and the desired size clumps can be isolated. When cell dissociation is partial, mechanical dissociation using the sharp edge of the pipette assisted with cutting and the isolation of the clumps.

An alternative approach was performed by the combined use of mechanical cutting of the colonies followed by isolation of the subcolonies by dispase. Cutting of the colonies was performed in PBS containing Ca and Mg. The sharp edge of micropipette was used to cut the colonies to clumps of about 100 cells. The pipette was also used to scrape and remove differentiated areas of the colonies. The PBS was then changed to regular prequilibrated human stem cells medium containing dispase (Gibco) 10 mg/ml and incubated for 5–10 minutes (at 37° C., 5% $CO_2$). As soon as the clumps were detached they were picked up by wide bore micro-pipette, washed in PBS containing Ca and Mg and transferred to a fresh feeder layer.

e) Human stem cell cryopreservation.

Early passage cells were cryo-preserved in clumps of about 100 cells by using the open pulled straw (OPS) vitrification method (Vajta et al 1998) with some modifications. French mini-straws (250 $\mu$l, IMV, L'Aigle, France) were heat-softened over a hot plate, and pulled manually until the inner diameter was reduced to about half of the original diameter. The straws were allowed to cool to room temperature and were than cut at the narrowest point with a razor blade. The straws were sterilised by gamma irradiation (15–25 K Gy). Two vitrification solutions (VS) were used. Both were based on a holding medium (HM) which included DMEM containing HEPES buffer (Gibco, without sodium pyruvate, glucose 4500 mg/L) supplemented with 20% fetal bovine serum (Hyclone, Logan, Utah). The first VS (VS1) included 10% dimethyl sulfoxide (DMSO, Sigma) and 10% ethylene glycol (EG, Sigma). The second vitrification solution (VS2) included 20% DMSO, 20% EG and 0.5M sucrose. All procedures were performed on a heating stage at 37° C. 4–6 clumps of ES cells were first incubated in VS1 for 1 minute followed by incubation in VS2 for 25 seconds. They were then washed in a 20 $\mu$l droplet of VS2 and placed within a droplet of 1–2 $\mu$l of VS2. The clumps were loaded into the narrow end of the straw from the droplet by capillary action. The narrow end was immediately submerged into liquid nitrogen. Straws were stored in liquid nitrogen. Thawing was also performed on a heating stage at 37° C. as previously described with slight modifications (Vatja et al 1998). Three seconds after removal from liquid nitrogen, the narrow end of the straw was submerged into HM supplemented with 0.2M sucrose. After 1 minute incubation the clumps were further incubated 5 minutes in HM with 0.1M sucrose and an additional 5 minutes in HM.

2. Stem cell characterization.

Colonies were fixed in the culture dishes by 100% ethanol for immuno-fluorescence demonstration of the stem cell surface markers GCTM-2, TRA 1–60 and SSEA-1, while 90% acetone fixation was used for SSEA-4. The sources of the monoclonal antibodies used for the detection of the markers were as follows: GCTM-2, this laboratory; TRA 1–60, a gift of Peter Andrews, University of Sheffield;

SSEA-1 (MC-480) and SSEA-4 (MC-813-70), Developmental Studies Hybridoma Bank, Iowa, Iowa. Antibody localisation was performed by using rabbit anti-mouse immunoglobulins conjugated to fluorescein isothiocyanate (Dako, Carpinteria, Calif.).

Alkaline phosphatase activity was demonstrated as previously described (Buehr M. and Mclaren A. Isolation and culture of primordial germ cells. *Methods Enzymol.* 225, 58–76, (1993)). Standard G-banding techniques were used for karyotyping.

3. Oct-4 expression studies.

To monitor expression of Oct-4, RT-PCR was carried out on colonies consisting predominantly of stem cells, or colonies which had undergone spontaneous differentiation as described below. mRNA was isolated on magnetic beads (Dynal AS, Oslo) following cell lysis according to the manufacturer's instructions, and solid-phase first strand cDNA synthesis was performed using Superscript II reverse transcriptase (Life Technologies). OCT-4 transcripts were assayed using the following primers: 5'-CGTTCTCTTTGGAAAGGTGTTC (forward) (SEQ ID NO: 1) and 3'-ACACTCGGACCACGTCTTTC (reverse) (SEQ ID NO: 2). As a control for mRNA quality, betaactin transcripts were assayed using the same RT-PCR and the following primers: 5'-CGCACCACTGGCATTGTCAT-3' (forward) (SEQ ID NO: 3), 5'-TTCTCCTTGATGTCACGCAC-3' (reverse) (SEQ ID NO: 4). Products were analyzed on a 1.5% agarose gel and visualized by ethidium bromide staining.

Colonies were cultured on mitotically inactivated mouse embryonic fibroblasts to confluency (about 3 weeks) and further on up to 7 weeks after passage. The medium was replaced every day. Alphafetoprotein and beta human chorionic gonadotropin levels were measured in medium conditioned by HES-1 and HES-2 at passage level 17 and 6 respectively. After 4–5 weeks of culture, conditioned medium was harvested 36 hours after last medium change, and the protein levels were determined by a specific immunoenzymometric assays (Eurogenetics, Tessenderilo, Belgium) and a fluorometric enzyme immunoassay (Dade, Miami, Fla.) respectively. These compounds were not detected in control medium conditioned only by feeder layer.

Differentiated cultures were fixed 6–7 weeks after passage (26—HES-1 and 9—HES-2) for immunofluorescence detection of lineage specific markers. After fixation with 100% ethanol, specific monoclonal antibodies were used to detect the 68 kDa neurofilament protein (Amersham, Amersham U.K), and neural cell adhesion molecule (Dako). Muscle specific actin and desmin were also detected by monoclonal antibodies (Dako) after fixation with methanol/acetone (1:1). Antibody localisation was performed as described above.

Clusters of cells destined to give rise to neural precursors were identified by their characteristic morphological features in central areas of ES cell colonies 2–3 weeks after plating. The clusters were dissected mechanically by a micropipette and replated in fresh serum free medium. Within 24 hours they formed spherical structures. The expression of the transcription factor PAX-6 and the intermediate filament nestin by these clusters was demonstrated by RT-PCR as described above. The following primers were used for PAX-6 and nestin respectively: Pax-6 forward primer, 5'AACAGACACAGCCCTCACAAACA3' (SEQ ID NO: 5); Pax-6 reverse primer, 5'CGGGAACTTGAACTGGAACTGAC3'(SEQ ID NO: 6); nestin forward primer, 5'CAGCTGGCGCACCTCAAGATG3' (SEQ ID NO: 7); nestin reverse primer, 5'AGGGAAGTTGGGCTCAGGACTGG3' (SEQ ID NO: 8).

The clusters were plated on poly-D-lysine (Sigma) and laminin (Sigma). They were fixed after 5 hours using 90% acetone in water for the immuno-fluorescence demonstration of N-CAM (Dako) while fixation with 4% paraformaldehyde in PBS was used to demonstrate nestin. Five days after plating, differentiated cells expending from the clusters were fixed with methanol for the immuno-fluorescence demonstration of NF160 KD (Boehringer Mannheim Biochemica) and with 4% paraformaldehyde in PBS for MAP 2a+b (Neomarkers, clone AP20), Antibody localisation was performed as described above.

5. Teratoma formation in Severe Combined Immunodeficient (SCID) mice.

At the time of routine passage, clumps of about 200 cells with an undifferentiated morphology were harvested as described above, and injected into the testis of 4–8 week old SCID mice (CB17 strain from the Walter and Eliza Hall Institute, Melbourne, Australia, 10–15 clumps/testis). 6–7 weeks later, the resulting tumours were fixed in neutral buffered formalin 10%, embedded in paraffin and examined histologically after hematoxylin and eosin staining.

EXAMPLES

Example 1

Derivation of Cell Lines HES-1 and HES-2

The outer trophectoderm layer was removed from four blastocysts by immunosurgery to isolate inner cell masses (ICM), which were then plated onto a feeder layer of mouse embryo fibroblasts (FIG. 3A). Within several days, groups of small, tightly packed cells had begun to proliferate from two of the four ICM. The small cells were mechanically dissociated from outgrowths of differentiated cells, and following replating they gave rise to flat colonies of cells with the morphological appearance of human EC or primate ES cells (FIG. 3B, C stem cell colonies). These colonies were further propagated by mechanically disaggregation to clumps which were replated onto fresh feeder cell layers. Growth from small clumps of cells (<10 cells) was not possible under the conditions of these cultures. Spontaneous differentiation, often yielding cells with the morphological appearance of early endoderm, was frequently observed during routine pass-age of the cells (FIG. 3D). Differentiation occurred rapidly if the cells were deprived of a feeder layer, even in the presence of LIF (FIG. 3E). While LIF was used during the early phases of the establishment of the cell lines, it was subsequently found to have no effect on the growth or differentiation of established cultures (not shown). Cell line HES-1 has been grown for 60 passages in vitro and HES-2 for 40 passages, corresponding to a minimum of approximately 360 and 90240 population doublings respectively, based on the average increase in colony size during routine passage, and both cell lines still consist mainly of cells with the morphology of ES cells. Both cell lines have been successfully recovered from cryopreservation.

Example 2

Marker Expression and Karyotype of the Human ES Cells

Marker and karyotype analysis were performed on HES-1 at passage levels 5–7, 14–18, 24–26 and 44–46, and on HES-2 at passage levels 6–8. ES cells contained alkaline phosphatase activity (FIG. 4A). Immunophenotyping of the ES cells was carried out using a series of antibodies which detect cell surface carbohydrates and associated proteins found on human EC cells. The ES cells reacted positively in indirect immunofluorescence assays with antibodies against the SSEA-4 and TRA 1–60 carbohydrate epitopes, and the staining patterns were similar to those observed in human EC cells (FIG. 4B, C). ES cells also reacted with monoclonal antibody GCTM-2, which detects an epitope on the protein core of a keratan sulphate/chondroitin sulphate pericellular matrix proteoglycan found in human EC cells (FIG. 4D). Like human EC cells, human ES cells did not express SSEA-1, a marker for mouse ES cells. Both cell lines were karyotypically normal and both were derived from female blastocysts.

Oct-4 is a POU domain transcription factor whose expression is limited in the mouse to pluripotent cells, and recent results show directly that zygotic expression of Oct-4 is essential for establishment of the pluripotent stem cell population of the inner cell mass. Oct-4 is also expressed in human EC cells and its expression is down regulated when these cells differentiate. Using RT-PCR to carry out mRNA analysis on isolated colonies consisting mainly of stem cells, we showed that human ES cells also express Oct-4 (FIG. 5, lanes 2–4). The PCR product was cloned and sequenced and shown to be identical to human Oct-4 (not shown).

Example 3
Differentiation of Human ES Cells In Vitro

Both cell lines underwent spontaneous differentiation under standard culture conditions, but the process of spontaneous differentiation could be accelerated by suboptimal culture conditions. Cultivation to high density for extended periods (4–7 weeks) without replacement of a feeder layer promoted differentiation of human ES cells. In high density cultures, expression of the stem cell marker Oct-4 was either undetectable or strongly downregulated relative to the levels of the housekeeping gene beta actin (FIG. 5, lanes 5–7). Alphafetoprotein and human chorionic gonadotrophin were readily detected by immunoassay in the supernatants of cultures grown to high density. Alphafetoprotein is a characteristic product of endoderm cells and may reflect either extraembryonic or embryonic endodermal differentiation; the levels observed (1210–5806 ng/ml) are indicative of extensive endoderm present. Human chorionic gonadotrophin secretion is characteristic of trophoblastic differentiation; the levels observed (6.4–54.6 IU/Liter) are consistent with a modest amount of differentiation along this lineage.

After prolonged cultivation at high density, multicellular aggregates or vesicular structures formed above the plane of the monolayer, and among these structures clusters of cells or single cells with elongated processes which extended out from their cell bodies, forming networks as they contacted other cells (FIG. 3F) were observed. The cells and the processes stained positively with antibodies against neurofilament proteins and the neural cell adhesion molecule (FIGS. 4E and F). Contracting muscle was seen infrequently in the cultures. While contracting muscle was a rare finding, bundles of cells which were stained positively with antibodies directed against muscle specific forms of actin, and less commonly cells containing desmin intermediate filaments (FIG. 6G and H) were often observed. In these high density cultures, there was no consistent pattern of structural organisation suggestive of the formation of embryoid bodies similar to those formed in mouse ES cell aggregates or arising sporadically in marmoset ES cell cultures.

Example 4
Differentiation of Human ES Cells in Xenografts

When HES-1 or HES-2 colonies of either early passage level (6; HES 1 and 2) or late passage level (HES-1, 14 and 27) were inoculated beneath the testis capsule of SCID mice, testicular lesions developed and were palpable from about 5 weeks after inoculation. All mice developed tumours, and in most cases both testis were affected. Upon autopsy lesions consisting of cystic masses filled with pale fluid and areas of solid tissue were observed. There was no gross evidence of metastatic spread to other sites within the peritoneal cavity. Histological examination revealed that the lesion had displaced the normal testis and contained solid areas of teratoma. Embryonal carcinoma was not observed in any lesion. All teratomas contained tissue representative of all three germ layers. Differentiated tissues seen included cartilage, squamous epithelium, primitive neuroectoderm, ganglionic structures, muscle, bone, and glandular epithelium (FIG. 6). Embryoid bodies were not observed in the xenografts.

Example 5
Identification and characterisation of neuronal progenitor cells and mature neuronal cells after induction of differentiation in vitro.

Differentiation was induced by culturing for prolonged periods and areas destined to give rise to neuronal cells cultures were identified by their characteristic morphology under phase microscopy or stereo microscopy. These aggregates of cells were isolated and replated into fresh serum free medium. They formed spherical structures. RT-PCR and immunofluorescence analysis showed that cells within these spheres expressed markers of primitive neuroectoderm including nestin, Pax-6 and polysialyated N-CAM. After cultivation for a brief period, cells migrated from the spheres onto the monolayer, where they acquired the morphological appearance of neurons; immunofluorescence analysis revealed that these cells expressed markers of mature neurons including the 160 kd neurofilament protein and MAP-2AB.

Example 6
Cryo-preservation of human ES cells.

Attempts to cryo-preserve human ES cells by using conventional slow freezing protocols were associated with a very poor outcome after thawing. Since ES cells are derived from the blastocyst and retain their embryonic properties in culture, we have postulated that cryopreservation by using a method which is efficient for embryos may be beneficial. Early passage clumps of human ES cells were frozen by using the open pulled straw (OPS) vitrification method which was recently shown to be highly efficient for the cryopreservation of bovine blastocysts (Vatja et al. 1998). Both cell lines were successfully thawed and further propagated for prolonged periods. The outcome of the vitrification procedure was further studied on cell line HES-1, and recovery of viable cells with this procedure was found to be highly efficient. All clumps (n=25) survived the procedure and attached and grew after thawing. Vitrification was associated with some cell death as evidenced by the reduced size of colonies originating from vitrified clumps two days after thawing in comparison to colonies from non-vitrified control clumps. However, two days in culture were sufficient to overcome this cell deficit, and 9 days after plating the size of colonies from frozen-thawed clumps exceeded that of control colonies at 7 days. Vitrification did not induce differentiation after thawing. Thawed cells retained a normal karyotype and the expression of primate stem cell markers, and formed teratomas in SCID mice.

Finally it is to be understood that various other modifications and/or alterations may be made without departing from the spirit of the present invention as outlined herein.

What is claimed is:

1. A method of modulating the differentiation of undifferentiated, pluripotent human embryonic stem (hES) cell in culture, comprising providing a fibroblast feeder layer which has been selected based on its ability to induce differentiation of undifferentiated, pluripotent human embryonic stem (hES) cells in culture, and growing said undifferentiated, pluripotent human embryonic stem (hES) cells on said fibroblast feeder layer, wherein said fibroblast feeder layer modulates the differentiation of said undifferentiated, pluripotent human embryonic stem (hES) cell in culture.

2. A method to of modulating the differentiation of undifferentiated, pluripotent human embryonic stem (hES) cell in culture, comprising providing a fibroblast feeder layer which has been selected based on its ability to favour differentiation of the hES cell into a somatic lineage or into an extraembryonic lineage, and growing said undifferentiated, pluripotent human embryonic stem (hES) cells on said fibroblast feeder layer, wherein said fibroblast feeder layer modulates the differentiation of said undifferentiated, pluripotent human embryonic stem (hES) cell in culture.

3. A method of modulating the differentiation of undifferentiated, pluripotent human embryonic stem (hES) cell in culture, comprising providing a fibroblast feeder layer which has been selected based on its ability to favour differentiation into a somatic lineage and to limit differentiation into an extraembryonic lineage, and growing said undifferentiated, pluripotent human embryonic stem (hES) cells on said fibroblast feeder layer, wherein said fibroblast feeder layer modulates the differentiation of said undifferentiated, pluripotent human embryonic stem (hES) cell in culture.

4. A method of modulating the differentiation of undifferentiated, pluripotent human embryonic stem (hES) cell in culture, comprising providing a fibroblast feeder layer which has been selected based on its ability to induce the differentiation of the hES cell into a somatic lineage or multiple somatic lineages, and growing said undifferentiated, pluripotent human embryonic stem (hES) cells on said fibroblast feeder layer, wherein said fibroblast feeder layer modulates the differentiation of said undifferentiated, pluripotent human embryonic stem (hES) cell in culture.

5. The method according to any one of claims 1–4, further comprising cultivating the hES cells for prolonged periods and/or at high density.

6. The method according to any one of claims 1–4, wherein the fibroblast feeder layer is a mouse and/or human fibroblast feeder layer.

7. The method according to any one of claims 1–4, wherein said fibroblast feeder layer comprises embryonic fibroblasts.

8. The method according to any one of claims 1–4, wherein the undifferentiated, pluripotent hES cells are prepared by a process comprising:

obtaining an in vitro fertilised human embryo and growing said embryo to a blastocyst stage of development;

removing inner cells mass (ICM) cells from said embryo;

culturing said ICM cells on the fibroblast feeder layer; and recovering the ICM cells from the feeder layer as hES cells.

* * * * *

SEQUENCE LISTING

<160> NUMBER OF SEQ ID NOS: 8

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: PCR primer

<400> SEQUENCE: 1
cgttctcttt ggaaaggtgt tc                                             22

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: PCR primer

<400> SEQUENCE: 2
acactcggac cacgtctttc                                                20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: PCR primer

<400> SEQUENCE: 3
cgcaccactg gcattgtcat                                                20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: PCR primer

<400> SEQUENCE: 4
ttctccttga tgtcacgcac                                                20

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence: PCR primer

<400> SEQUENCE: 5
aacagacaca gccctcacaa aca                                            23

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: PCR primer

<400> SEQUENCE: 6
cgggaacttg aactggaact gac                                            23

<210> SEQ ID NO 7
<211> LENGTH: 21

-continued

```
<212> TYPE: DNA
<213> ORGANISM: Artificial Sequence
<220> FEATURE:
<223> OTHER INFORMATION: Description of Artificial Sequence: PCR primer

<400> SEQUENCE: 7
cagctggcgc acctcaagat g                                              21

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence: PCR primer

<400> SEQUENCE: 8
agggaagttg ggctcaggac tgg                                            23
```